United States Patent
Wensheng et al.

(10) Patent No.: US 8,334,388 B2
(45) Date of Patent: Dec. 18, 2012

(54) PALONOSETRON SALTS AND PROCESSES FOR PREPARATION AND PURIFICATION THEREOF

(75) Inventors: Tang Wensheng, Shanghai (CN); Zhang Xingzhong, Shanxi Province (CN); He Xungui, Shanghai (CN); Yuan Wang, Shanghai (CN); Joseph Kaspi, Givatayim (IL)

(73) Assignee: Chemagis Ltd., Bnei Brak (IL)

( * ) Notice: Subject to any disclaimer, the term of this patent is extended or adjusted under 35 U.S.C. 154(b) by 437 days.

(21) Appl. No.: 12/601,744

(22) PCT Filed: May 28, 2008

(86) PCT No.: PCT/IL2008/000720
§ 371 (c)(1),
(2), (4) Date: Jan. 14, 2010

(87) PCT Pub. No.: WO2008/146283
PCT Pub. Date: Apr. 12, 2008

(65) Prior Publication Data
US 2010/0174080 A1    Jul. 8, 2010

Related U.S. Application Data

(60) Provisional application No. 60/932,139, filed on May 29, 2007.

(51) Int. Cl.
*C07D 453/02* (2006.01)
(52) U.S. Cl. ........................................ 546/133
(58) Field of Classification Search ............... 546/133
See application file for complete search history.

(56) References Cited

U.S. PATENT DOCUMENTS

| 5,202,333 A | 4/1993 | Berger et al. |
| 5,510,486 A | 4/1996 | Robinson, III et al. |
| 5,567,818 A | 10/1996 | Kowalczyk et al. |

FOREIGN PATENT DOCUMENTS
WO   WO 2009136405   * 11/2009

OTHER PUBLICATIONS

U.S. Patent & Trademark Office, International Search Report in International Patent Application No. PCT/IL2008/00720 (Jan. 6, 2009).

* cited by examiner

*Primary Examiner* — Nizal Chandrakumar
(74) *Attorney, Agent, or Firm* — Leydig, Voit & Mayer, Ltd.

(57) ABSTRACT

Provided are novel salts of 2-(1-azabicyclo-[2.2.2]oct-3-yl)-2,3,3a,4,5,6-hexahydro-1H-benz[de]isoquinolin-1-one, methods of using such salts, and processes for producing such salts.

5 Claims, No Drawings

PALONOSETRON SALTS AND PROCESSES FOR PREPARATION AND PURIFICATION THEREOF

CROSS-REFERENCE TO RELATED APPLICATIONS

This patent application is the U.S. national phase of International Patent Application No. PCT/IL2008/000720, filed May 28, 2008, which claims the benefit of U.S. Provisional Patent Application No. 60/932,139, filed May 29, 2007, all of which are incorporated herein by reference in their entirety for all purposes.

TECHNICAL FIELD

The present invention relates to organic chemistry and more particularly to processes for preparation and purification of palonosetron and salts thereof.

BACKGROUND OF THE INVENTION

Palonosetron, 2-(1-azabicyclo-[2.2.2]oct-3S-yl)-2,3,3aS, 4,5,6-hexahydro-1H-benz[de]isoquinolin-1-one (Compound A), has the following structural formula, which demonstrates that the compound has two chiral centers. The most active palonosetron isomer has both chiral centers in the S-configuration.

Compound A

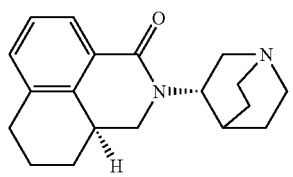

Palonosetron hydrochloride is marketed as ALOXI® and is a selective 5-HT₃ receptor antagonist developed for the prevention of both acute and delayed chemotherapy-induced nausea and vomiting (CINV) caused by moderately emetogenic chemotherapy. Palonosetron hydrochloride was approved by the U.S. Food and Drug Administration (FDA) on Jul. 25, 2003, and was commercially launched in September 2003. Palonosetron hydrochloride also is used for treating emesis, which is a gastrointestinal disorder treatable with prokinetic agents, and for treating patients recovering from surgical anesthesia or undergoing a drug therapy whenever a significant side effect is emesis. The recommended dosage of palonosetron is 0.25 mg, which is administered as a single dose about 30 minutes before starting chemotherapy.

The synthetic route for preparing palonosetron is described in U.S. Pat. No. 5,202,333, wherein 5,6,7,8-tetrahydro-1-naphthalenecarboxylic acid (Compound II) is reacted with (S)-3-amino-1-azabicyclo[2.2.2]octane (Compound III) to obtain (S)—N-(1-azabicyclo-[2.2.2]oct-3-yl)-5,6,7,8-tetrahydro-1-naphthalenecarboxamide (Compound IV), which is recrystallized from a mixture of ethyl acetate and hexane. Reaction of Compound IV with n-butyl lithium in hexane in presence of dimethylformamide (DMF) affords (S)-2-(1-azabicyclo-[2.2.2]oct-3-yl)-2,4,5,6-tetrahydro-1H-benz[de]isoquinolin-1-one (Compound V), and treatment of Compound V using palladium hydroxide on carbon with hydrogen affords a diastereomeric mixture containing 98.9% of Compound A. This process is depicted in Scheme 1 below.

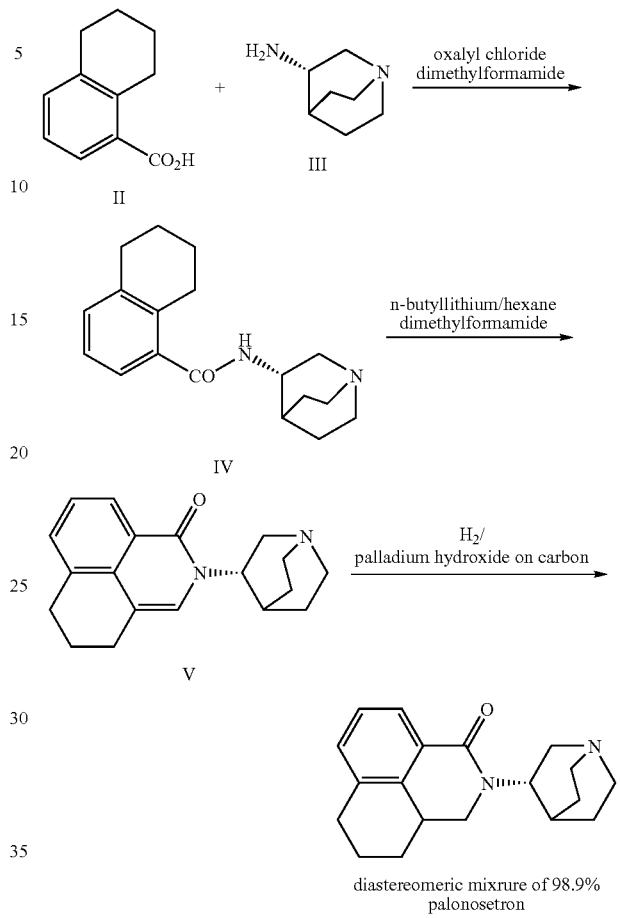

U.S. Pat. No. 5,510,486 (the '486 patent) discloses other processes for preparing palonosetron, the pharmaceutically acceptable hydrochloride salt, individual stereoisomers, and mixture of stereoisomers thereof, as illustrated in Scheme 2 below.

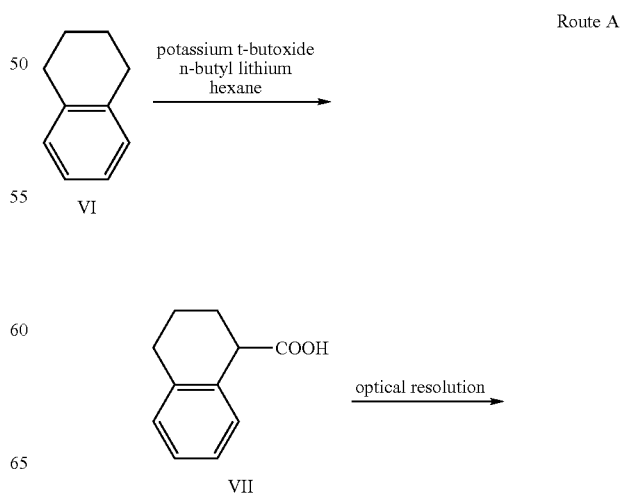

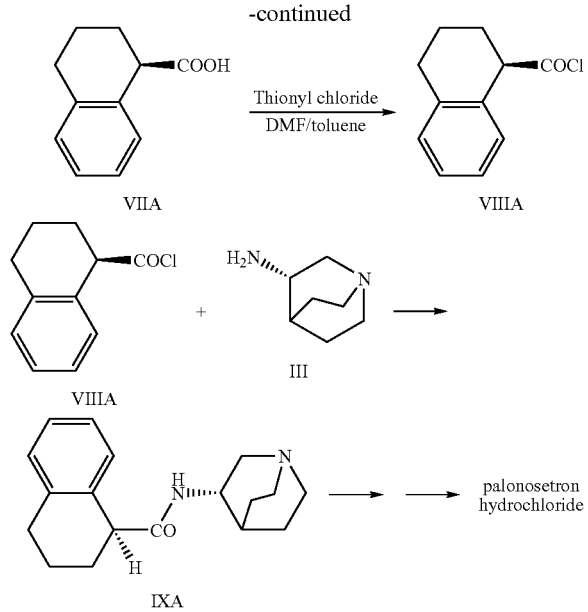

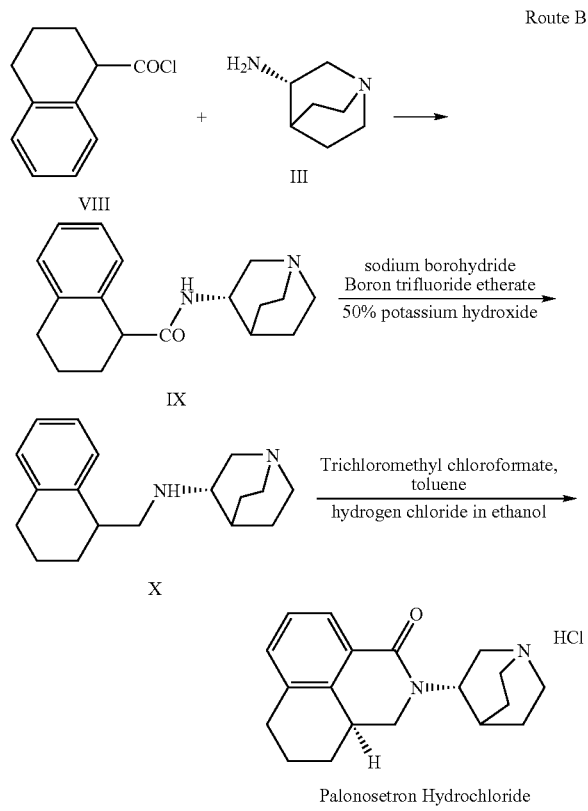

According to Route A, 1,2,3,4-tetrahydronaphthalene (Compound VI) is converted into 1,2,3,4-tetrahydro-1-naphthoic acid (Compound VII), which is optically resolved to obtain the S-enantiomer (Compound VIIA). The optically enriched acid then is reacted with thionyl chloride to afford (S)-1,2,3,4-tetrahydro-1-naphthoyl chloride (Compound VIIIA). This acid chloride is reacted with Compound III to afford N-(1-azabicyclo[2.2.2]oct-3S-yl)-(1,2,3,4-tetrahydronaphthalen-1S-ylmethyl)amine (Compound IXA), which subsequently is converted to palonosetron hydrochloride over several steps.

According to Route B, 1,2,3,4-tetrahydro-1-naphthoic acid chloride (Compound VIII) is reacted with Compound III to give N-(1-azabicyclo[2.2.2]oct-3S-yl)-1,2,3,4-tetrahydronaphthalen-1-ylcarboxamide (Compound IX). The amide then is reduced to give (1-azabicyclo[2.2.2]oct-3S-yl)-(1,2,3,4-tetrahydronaphthalen-1S-ylmethyl)amine (Compound X). The resulting amine is reacted with a formylating agent, then treated with a Lewis acid to afford 2-(1-azabicyclo[2.2.2]oct-S-yl)-2,3,aS,4,5,6-hexahydro-1H-benz[de]isoquinolin-1-one as a diastereomeric mixture. This diastereomeric mixture is separated into individual stereoisomers or mixtures of stereoisomers with the desired stereomer, then converted to the hydrochloride salt of palonosetron. The '486 patent (in example 6) discloses a melting point of 303° C. and $[\alpha]_D = 90°$ (c=1, chloroform). However, based on the previous data, this may be a typographical error and the optical rotation apparently should be $[\alpha]_D = -90°$ for the obtained palonosetron hydrochloride.

U.S. Pat. No. 5,567,818 discloses other processes for preparing palonosetron, palonosetron hydrochloride, individual stereoisomers thereof, and mixtures of stereoisomers thereof (Scheme 3).

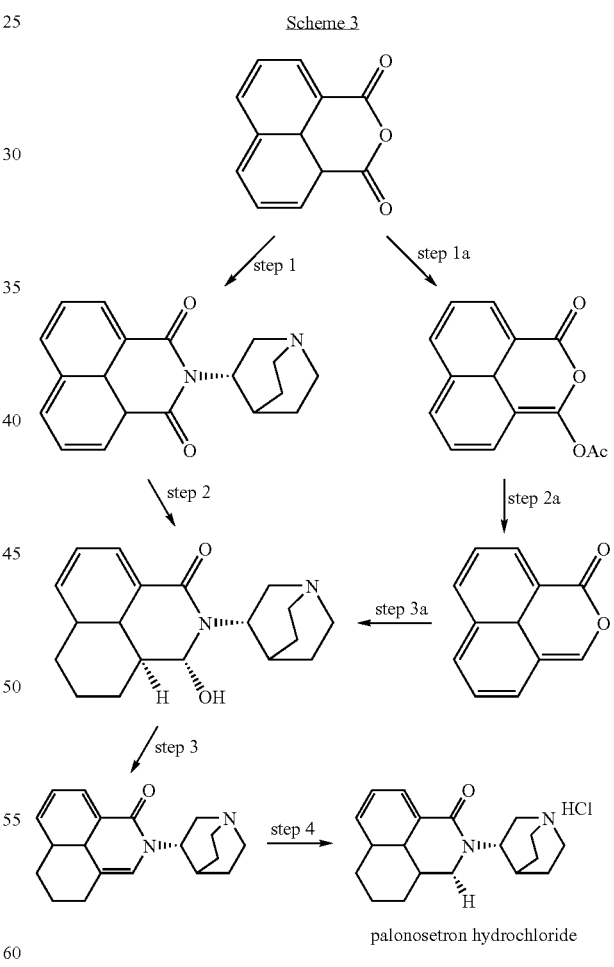

The starting material 1,8-naphthalenic anhydride is reacted with (S)-1-azabicyclo[2.2.2]-oct-3-ylamine in isopropanol to obtain (S)-2-(1-azabicyclo[2.2.2]oct-3-yl)-2,3-dihydro-1H-benz[de]isoquinolin-1,3-dione, which is purified by flash chromatography, in step 1 of Scheme 3. In step 2, the product is reduced under hydrogen atmosphere to obtain 2-(1-azabicyclo[2.2.2]oct-3S-yl)-3-hydroxy-2,3,3a,4,5,6-hexahydro-1H-benz[de]isoquinolin-1-one as a foam. In step 3, the product of step 2 is treated under acidic conditions to provide the dehydration product (S)-2-(1-azabicyclo[2.2.2]oct-3-yl)-2,4,5,6-tetrahydro-1H-benz[de]isoquinolin-1-one hydrochloride. In step 4, the dehydration product is hydrogenated to obtain a 7:3 mixture of diastereomers of palonosetron hydrochloride (70% of 2-(1-azabicyclo-[2.2.2]oct-3S-yl)-2,3,3aS,4,5,6-hexahydro-1H-benz[de]isoquinolin-1-one and 30% of 2-(1-azabicyclo-[2.2.2]oct-3S-yl)-2,3,3aR,4,5,6-hexahydro-1H-benz[de]isoquinolin-1-one). Selective precipitation afforded 97% of the preferred stereoisomer, Compound A, and 3% of the less preferred isomer, Compound B, (2-(1-azabicyclo-[2.2.2]oct-3S-yl)-2,3,3aR,4,5,6-hexahydro-1H-benz[de]isoquinolin-1-one). The diastereomeric mixture of 97% Compound A and 3% Compound B was further purified via recrystallization to obtain 99.1% Compound A, with a melting point of 303° C. and $[\alpha]_D = -90.4°$ (c=1, chloroform)

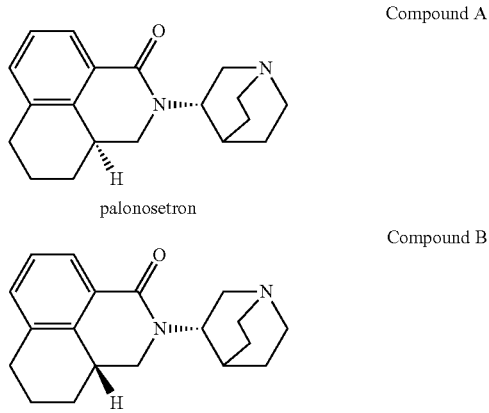

Compound A palonosetron

Compound B

In an alternative process, the compound 2-(1-azabicyclo-[2.2.2]oct-3S-yl)-3-hydroxy-2,3,3a,4,5,6-hexahydro-1H-benz[de]isoquinolin-1-one is obtained via the intermediate 2-oxa-2,4,5,6-tetrahydrobenz[de]naphthal-1-one, as demonstrated in steps 1a-3a of Scheme 3, above.

Usually, the minimal purity of a drug, as mandated by the appropriate regional or national regulative authorities (e.g., the FDA) is at least 99.5%. However, the purity and composition A/B isomer ratio in which the palonosetron hydrochloride is obtained are relatively low (i.e., 99.1% and 97/3, respectively).

Therefore a need still exists in the art for methods of preparing palonosetron and salts thereof, which can be obtained in a single crystallization having higher purity and A/B isomer ratio, which meet the regulatory standards of the various regulating agencies.

SUMMARY OF THE INVENTION

The present invention is directed to methods of preparing palonosetron, i.e., (2-(1-azabicyclo-[2.2.2]oct-3-yl)-2,3,3a,4,5,6-hexahydro-1H-benz[de]isoquinolin-1-one), and salts thereof having a high purity and a high isomeric ratio. The (3S),(3aS) isomer of 2-(1-azabicyclo-[2.2.2]oct-3-yl)-2,3,3a,4,5,6-hexahydro-1H-benz[de]isoquinolin-1-one (palonosetron) is alternatively referred to as Compound A throughout this disclosure. The (3S),(3aR) isomer is alternatively referred to as Compound B throughout this disclosure.

As used throughout, Compound A and Compound B can refer to the free base or salt form, unless the context indicates otherwise.

Thus, one aspect of the invention is to provide a method of preparing pure palonosetron salt comprising:
  (a) dissolving or partially dissolving impure palonosetron in an organic solvent;
  (b) optionally cooling the solution or partial solution of step (a) to a temperature below 20° C.; and
  (c) admixing an acid and the solution of step (a) or step (b) to form crystals of pure palonosetron salt, which is different from the HCl salt;
wherein the impure palonosetron has a purity of up to 99.1% and an isomer ratio of up to 97:3 Compound A:Compound B and the pure palonosetron salt has a purity of at least 99.5% and an isomer ratio of 99:1 or greater.

In some embodiments, the process further comprises (d) collecting the crystals of pure palonosetron salt. In certain embodiments, the collecting is via filtration, but other means of collecting can be employed, such as decanting. In various embodiments, the collected crystals can be further washed and dried.

In various cases, the acid used in step (c) is an organic acid such as oxalic acid or an inorganic acid, such as hydrobromic acid. The acid of step (c) determines the palonosetron salt prepared. For example, use of hydrobromic acid results in the hydrobromide salt; use of oxalic acid results in the oxalate salt. In preferred embodiments, the palonosetron salt prepared is one of the following: oxalate salt, benzoate salt, maleate salt, malonate salt, fumarate salt, tartrate salt, succinate salt, citrate salt, mesylate salt, hydrobromide salt, hydroiodide salt, or phosphate salt. The hydrochloric salt is not preferred.

Another aspect of the invention is to provide a method of purifying a palonosetron salt comprising:
  (a) dissolving or partially dissolving an impure Compound A in at least one organic solvent;
  (b) optionally heating the solution or partial solution of step (a) to a temperature greater than 30° C.;
  (c) cooling the solution or partial solution of step (a) or step (b) to a temperature below 20° C. for a time sufficient to permit crystallization of the pure salt of Compound A; wherein the impure salt of Compound A has a purity of up to 99.1% and an isomer ratio (of Compound A:Compound B) of up to 97:3, and the pure salt of Compound A has a purity of at least 99.5% and an isomer ratio of 99:1 or greater.

In some embodiments, the purification of the salt of Compound A further comprises collecting the crystals of the pure salt of Compound A by filtration, washing and drying.

Yet another aspect of the invention is to provide a method of preparing palonosetron base from a Compound A salt, comprising:
  (a) admixing the Compound A salt with an organic solvent and water and adding a base to form the palonosetron base and an organic layer and an aqueous layer;
  (b) separating the organic layer from the aqueous layer, wherein at least a portion of the palonosetron base is in the organic layer; and
  (c) extracting the aqueous layer with a second organic solvent to isolate palonosetron base in the organic solvent.

DETAILED DESCRIPTION OF THE INVENTION

The present invention provides salts of 2-(1-azabicyclo-[2.2.2]oct-3-yl)-2,3,3a,4,5,6-hexahydro-1H-benz[de]isoquinolin-1-one in high purity and isomer ratio. In some embodiments, the 2-(1-azabicyclo-[2.2.2]oct-3-yl)-2,3,3a,4,5,6-hexahydro-1H-benz[de]isoquinolin-1-one is (3S),(3aS) palonosetron (Compound A), while in other embodiments, the 2-(1-azabicyclo-[2.2.2]oct-3-yl)-2,3,3a,4,5,6-hexahydro-1H-benz[de]isoquinolin-1-one is the (3S),(3aR) isomer (Compound B). The salt of 2-(1-azabicyclo-[2.2.2]oct-3-yl)-2,3,3a,4,5,6-hexahydro-1H-benz[de]isoquinolin-1-one can be, but is not limited to, the oxalate salt, benzoate salt, maleate salt, malonate salt, fumarate salt, tartrate salt, succinate salt, citrate salt, mesylate salt, hydrobromide salt, hydroiodide salt or phosphate salt.

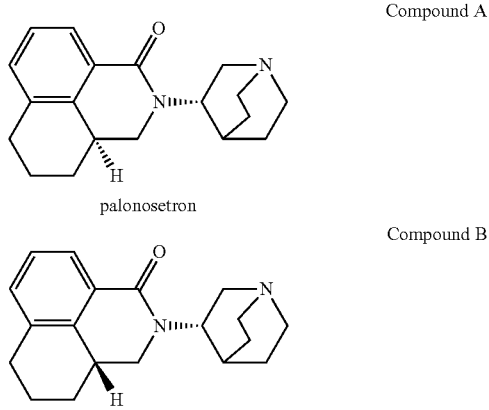

palonosetron

Compound A

Compound B

As used herein, the terms "purity" or "pure" refers to the amount of a particular compound in a mixture. Pure Compound A is a sample of Compound A having at least 99.5% Compound A by weight of the sample, wherein the other 0.5% or less by weight are different compounds, which typically includes or comprises Compound B. Impure Compound A is a sample of Compound A having up to 99.1% Compound A and the remainder of the sample, 0.9% by weight or greater, is a different compound or mixture of compounds, which typically includes or comprises Compound B. Pure and impure Compound B are similarly defined. The purity of a sample can be determined by known analytical techniques, such as high pressure/high performance liquid chromatography (HPLC), gas chromatography (GC), and the like. In various embodiments, the pure palonosetron or salt thereof has a purity of 99.6% or greater, 99.7% or greater, 99.8% or greater, or 99.9% or greater.

The term "isomer ratio," as used herein, is the molar ratio of (3S),(3aS) isomer to (3S),(3aR) isomer of 2-(1-azabicyclo-[2.2.2]oct-3-yl)-2,3,3a,4,5,6-hexahydro-1H-benz[de]isoquinolin-1-one. Thus, a sample of Compound A having a 97:3 isomer ratio has 97% Compound A and 3% Compound B, i.e., an A/B ratio of 97/3.

Salts of Compound A or Compound B can be prepared by methods known in the art for preparing acid addition salts of active pharmaceutical ingredients, e.g., by treating the active pharmaceutical ingredient (e.g., in the form of its free base) with a suitable acid to obtain the salt form. Exemplary salts of Compound A of the present invention include, but are not limited to, crystalline forms of one or more of the following: oxalate salt, benzoate salt, maleate salt, fumarate salt, tartrate salt, succinate salt, citrate salt, mesylate salt, hydrobromide salt, or phosphate salt. Exemplary salts of Compound B of the present invention include, but are not limited to, the crystalline form of the hydroiodide salt.

It has been discovered that crystallizing 2-(1-azabicyclo-[2.2.2]oct-3-yl)-2,3,3a,4,5,6-hexahydro-1H-benz[de]isoquinolin-1-one base from a solution containing an acid, such as hydrobromic acid (HBr), provides a salt of palonosetron that has a greater purity and/or isomer ratio than the starting material. The maleate salt, succinic acid salt, citric acid salt, and methanesulfonic acid salt show relatively high selectivity for Compound A versus Compound B when crystallizing. On the other hand, while crystallizing 2-(1-azabicyclo-[2.2.2]oct-3-yl)-2,3,3a,4,5,6-hexahydro-1H-benz[de]isoquinolin-1-one base from a solution containing hydroiodic acid (HI), a Compound B salt was surprisingly predominantly obtained. Thus, the use of Compound B hydroiodide salt (having the opposite configuration at the 3a-position) can be advantageous, e.g., as a marker for testing the optical purity of a palonosetron sample.

The salts of Compound A (palonosetron) of the present invention can be prepared by any suitable process, e.g., by mixing 2-(1-azabicyclo-[2.2.2]oct-3-yl)-2,3,3a,4,5,6-hexahydro-1H-benz[de]isoquinolin-1-one base, obtained by any suitable method known in the art, with an organic solvent, e.g., a $C_1$-$C_4$ alcohol such as ethanol, optionally cooling (e.g., to a temperature less than 20°, or, preferably about 10° C.), adding an organic or an inorganic acid and isolating the crystals by any suitable method, e.g., filtration.

Disclosed herein is a process for preparing a salt of palonosetron comprising:
(a) dissolving or partially dissolving 2-(1-azabicyclo-[2.2.2]oct-3-yl)-2,3,3a,4,5,6-hexahydro-1H-benz[de]isoquinolin-1-one base in an organic solvent;
(b) optionally cooling the solution or partial solution of step (a) to a temperature less than 20° C.; and
(c) adding an acid to the solution or partial solution of step (a) or (b) to form crystals of a salt of palonosetron, which is different from the HCl salt.

In some embodiments, the method further comprises collecting the crystals by filtration and/or washing and drying the crystals.

The term "dissolving" or "partially dissolving" as used herein refers to preparing a solution of the 2-(1-azabicyclo-[2.2.2]oct-3-yl)-2,3,3a,4,5,6-hexahydro-1H-benz[de]isoquinolin-1-one base, salt, or mixture in an organic solvent. In cases where the base does not fully dissolve in the organic solvent, the resulting mixture is a partial solution.

The organic solvent which can dissolve or partially dissolve the 2-(1-azabicyclo-[2.2.2]oct-3-yl)-2,3,3a,4,5,6-hexahydro-1H-benz[de]isoquinolin-1-one or salt thereof can be, for example, a lower $C_1$-$C_4$ alkyl alcohol, like methanol, ethanol, n-propanol, isopropanol, or mixtures thereof. In a preferred embodiment, the organic solvent comprises ethanol.

The acid can be either an organic or inorganic acid and can be oxalic acid, benzoic acid, maleic acid, malonic acid, fumaric acid, tartaric acid, succinic acid, citric acid, acetic acid, sulfuric acid, phosphorous acid, lactic acid, tartaric acid, gluconic acid, benzene sulfonic acid, p-toluenesulfonic acid, methanesulfonic acid, hydrobromic acid, hydroiodic acid, or phosphoric acid.

Novel salts of Compound A or Compound B have been obtained in high purities using the disclosed methods. Table 1 demonstrates comparative results showing that the purity of the hydrobromide salt of Compound A after only one crystallization was sufficient for pharmaceutical usage (i.e., >99.5%), wherein the hydrochloride salt of Compound A was not sufficiently pure after 2 recrystallizations.

TABLE 1

| Status | The hydrochloride salt of Compound A | | The hydrobromide salt of Compound A | |
| --- | --- | --- | --- | --- |
| | Yield | Purity, A/B isomer ratio | Yield | Purity, A/B isomer ratio |
| Crude | 25.5% | 98.8% 79/20 | 61% | 99.2% 77/22 |
| First Recrystallization | 56% | 99.2% 98.2/1.1 | 83% | >99.9% 97/2 |
| Second Recrystallization | 70% | 99.4% 99.7/0.2 | 80% | >99.9% 99.2/0.72 |

The purities were determined by HPLC

According to the data in Table 1, when crude Compound A hydrobromide salt, having a purity of about 99.2% and A/B isomer ration of 77/22 (by HPLC), was crystallized from ethanol, a product having greater than 99.9% purity and A/B isomer ration of 97/2 was obtained. Upon a second crystallization, the A/B isomer ratio was improved to 99.2/0.72. Thus, the recrystallization of the hydrobromide salt of Compound A was found to provide Compound A in higher purity, similar or greater isomer ratio, and a much better yield than the hydrochloride salt of Compound A. Thus, the salts of Compound A can be obtained in high yield, e.g., the hydrobromide salt of Compound A is obtained in 83% yield, having a purity of 99.9%.

The conversion of 2-(1-azabicyclo-[2.2.2]oct-3-yl)-2,3,3a,4,5,6-hexahydro-1H-benz[de]isoquinolin-1-one base to an acid addition salt can serve as a convenient process for the purification of palonosetron, which may be optionally converted to palonosetron hydrochloride. Thus, the present invention further provides a process for purifying an impure salt of Compound A by crystallization, which process preferably includes:

(a) dissolving or partially dissolving the impure salt of Compound A in at least one organic solvent;
(b) optionally heating the solution or partial solution of step (a) to a temperature greater than 30° C.; and
(c) cooling the solution or partial solution of step (a) or step (b) for a time sufficient to allow crystallization of the pure salt of Compound A, wherein the impure salt of Compound A has a purity of up to 99.1% by weight and an isomer ratio of up to 97:3 Compound A:Compound B, and the pure salt of Compound A has a purity of at least 99.5% by weight and an isomer ratio of 99:1 or greater. In some embodiments, the process further comprises collecting the crystals of the pure salt of Compound A, and/or washing and drying the crystals.

The at least one organic solvent can be methanol, ethanol, n-propanol, isopropanol, dichloromethane, chloroform, n-pentane, n-hexane, cyclohexane, n-heptane, petroleum ether, or mixtures thereof. In a preferred embodiment, the solvents or solvent mixtures comprise ethanol and/or a 1:1:1 (by volume) mixture of methanol:dichloromethane:petroleum ether.

The present invention further provides a method of preparing palonosetron base in high yield from a salt of Compound A, comprising:

(a) admixing a salt of Compound A with an organic solvent and water and adding a base to form the palonosetron base, an organic layer and an aqueous layer;
(b) separating the organic layer from the aqueous layer, wherein at least a portion of the palonosetron base is in the organic layer; and
(c) extracting the aqueous layer with a second organic solvent to isolate palonosetron base in the organic solvent.

In accordance with the present invention, exemplary organic solvents include, but are not limited to, methanol, ethanol, n-propanol, isopropanol, methyl acetate, ethyl acetate, n-propyl acetate, isopropyl acetate, n-butyl acetate, isobutyl acetate, chloroform, dichloromethane and mixtures thereof. A preferred organic solvent is a mixture of ethyl acetate and methanol. The preferred ratio between ethyl acetate and methanol in the solvent mixture is 50/8 (v/v).

Exemplary bases can include, but are not limited to, lithium hydroxide, sodium hydroxide, potassium hydroxide, sodium carbonate, potassium carbonate, and combinations thereof. A preferred base is sodium hydroxide.

The palonosetron base can be obtained from the salt of Compound A in a yield higher than 99%.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless, otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Although, the following examples illustrate the practice of the present invention in some of its embodiments, the examples should not be construed as limiting the scope of the invention. Other embodiments will be apparent to one skilled in the art from consideration of the specification and examples. It is intended that the specification, including the examples, is considered exemplary only without limiting the scope and spirit of the invention.

EXAMPLES

Example 1

Reference Example

This example describes the preparation of palonosetron hydrochloride by reaction of N-(1-azabicyclo[2.2.2]oct-3S-yl)-1,2,3,4-tetrahydro-naphthalene-1S-ylmethylamine with trichloromethyl chloroformate, according to example in U.S. Pat. No. 5,202,333.

A reaction vessel was charged with a solution of N-(1-azabicyclo-[2.2.2]oct-3S-yl)-1,2,3,4-tetrahydronaphthalene-1S-ylmethylamine (80.15 g, 0.3 mole) in toluene (810 ml). Trichloromethyl chloroformate (25.3 ml, 8.3M, 0.21 mol) in toluene (100 ml) was added at such a rate so as to maintain the temperature below 50° C. The mixture was stirred for 18 hours, then boron trifluoride etherate was added (110.3 ml, 8.1M, 0.89 mol). The mixture was refluxed for 5 hours. The mixture then was cooled to 30° C., and 2N hydrochloric acid and water (455 ml) were added. The mixture was heated to reflux for 1 hour and then the solution was cooled to about 10° C. Potassium hydroxide was added (200 g, 50% in water) at such a rate so as to maintain the temperature below 40° C. The mixture was added to ethyl acetate (800 ml) and filtered. The aqueous layer was separated and extracted with ethyl acetate (2×600 ml). The combined ethyl acetate layers were concentrated and the resulting residue was dissolved in isopropanol (1080 ml). The solution was treated with 4N hydrochloric acid in ethanol and cooled to about 2-3° C. The precipitate was collected by filtration, washed with ethanol, and dried to afford dry palonosetron hydrochloride (25.5 grams, 0.077 mol, 25.5% yield) having 98.8% purity and A/B isomer ratio of 79/20. The crude palonostron hydrochloride was crystallized to obtain 14.3 g of palonostron hydrochloride in 56% yield having purity of 99.2% and A/B isomer ratio of 98.2/1.1. A second crystallization afforded 10 g of palonostron hydrochloride in 70% yield having 99.4% purity and A/B isomer ratio of 99.7/0.2, and third crystallization afforded 5 g of palonostron hydrochloride in 50% yield having purity of 99.5% and A/B isomer ratio of 99.9/0.027.

Example 2

Hydroiodide Salt of Compound B 2-(1-azabicyclo-[2.2.2]oct-3-yl)-2,3,3a,4,5,6-hexahydro-1H-benz[de]isoquinolin-1-one base (18 gram, 0.0607 mol), having an A/B isomer ratio of 30/64, was suspended in absolute ethanol (180 ml). The mixture was cooled to a temperature of 10° C. Hydriodic acid (14.4 grams, 55-58%, 0.062 mmol) then was added drop-wise. The mixture was stirred at a temperature of 10° C. for about an hour and concentrated under vacuum. The residue then was diluted with ethanol (50 ml) and mixed for about an hour at 10° C. The resulting solid was filtered and dried under reduced pressure to afford the hydroiodide of Compound B (8.6 g, 57% yield) having an A/B isomer ratio of 21/78 and purity of 97.4%. The obtained hydroiodide salt was mixed with a (1:1:1 by volume) mixture of methanol:dichloromethane:petroleum ether and heated to reflux to form a solution. The mixture was left to cool to room temperature and stirred at room temperature for about an hour. Then, the mixture was cooled to about 5° C. and stirred at that temperature for about an hour. The resulting crystals were filtered, washed with cold (1:1 by volume) mixture of methanol:dichloromethane and dried to afford (4.3 g, 54% yield) of the hydroiodide salt of Compound B having A/B isomer ratio of 2.6/97.3, melting point of 245-248° C., and purity of 99.7%.

Example 3

Hydrobromide Salt of Palonosetron 2-(1-azabicyclo-[2.2.2]oct-3-yl)-2,3,3a,4,5,6-hexahydro-1H-benz[de]isoquinolin-1-one base (30.2 gram, 0.102 mol) was mixed with absolute ethanol (200 ml). The mixture was cooled to about 10° C. and 40% hydrobromic acid (HBr) was added dropwise (23 ml, 0.111 mol). The mixture was stirred at 10° C. for one hour, then concentrated in vacuo. The residue was diluted with ethanol (50 ml) and stirred at 10° C. for one hour. The resulting solid was filtered and dried under reduced pressure to afford 23.1 g of the hydrobromide salt of palonosetron (61% yield) having A/B isomer ratio of 77/22 and purity of 99.2% (as determined by HPLC).

The crude hydrobromide salt (22 g, 0.058 mol) was mixed with ethanol (835 ml) and the mixture was heated to reflux to obtain a solution and filtered. The filtrate was cooled to 10° C. and stirred at that temperature overnight to affect crystallization. The resulting crystals were filtered off to obtain 18.2 g of the hydrobromide salt in 83% yield having purity of over 99.9% (by HPLC) and A/B isomer ratio of 97/2. Further crystallization afforded 14.6 g of the hydrobromide salt of palonosetron in 80% yield having AB isomer ratio of 99.2/0.72.

Examples 4-10

Other Salts of Palonosetron

Preparation of other salts of palonosetron was carried out using the procedure of example 3. The resulting isomer ratios are listed in Table 2, below. In all the examples, 1 g of 2-(1-azabicyclo-[2.2.2]oct-3-yl)-2,3,3a,4,5,6-hexahydro-1H-benz[de]isoquinolin-1-one base was used per 10 ml ethanol, except for the fumarate salt, where 1 g of the base was used per 25 ml ethanol.

TABLE 2

| Example | Salt | A/B isomer ratio before recrysallization | A/B isomer ratio after recrystallization |
|---|---|---|---|
| 4 | Fumarate | 47/52 | 59/37 |
| 5 | Maleate | 47/52 | 84/15 |
| 6 | Citrate | 47/52 | 78/21 |
| 7 | Tartrate | 47/52 | 66/39 |
| 8 | Succinate | 47/52 | 82/17 |
| 9 | Mesylate | 47/52 | 84/15 |
| 10 | Phosphate | 47/52 | 48/47 |

Example 11

Palonosetron Base from Palonosetron Hydrobromide

The hydrobromide salt of palonosetron (19 g, 50.5 mmol) was mixed with ethyl acetate (100 ml), methanol (16 ml) and water (100 ml). Then, sodium hydroxide (2.5 g) was added, and the mixture was stirred for one hour. The organic and aqueous layers were separated, and the aqueous layer was washed twice with a mixture of 50/8 ethyl acetate/methanol (v/v). The combined organic phase was concentrated under vacuum to afford 15 g of palonosetron base in 99.9% yield.

What is claimed:

1. A method of purifying a palonosetron hydrobromide salt comprising:
   (a) dissolving or partially dissolving an impure (3S),(3aS) palonosetron hydrobromide salt in at least one organic solvent;
   (b) optionally heating the solution or partial solution of step (a) to a temperature greater than 30° C.; and
   (c) cooling the solution or partial solution of step (a) or step (b) to a temperature below 20° C. for a time sufficient to permit crystallization of the pure salt of (3S),(3aS) palonosetron, wherein the impure salt of (3S),(3aS) isomer has a purity of up to 99.1% and an isomer ratio of (3S),(3aS) isomer:(3S),(3aR) isomer of up to 97:3, and the pure salt of palonosetron has a purity of at least 99.5% and an isomer ratio of 99:1 or greater.

2. The method of claim 1, further comprising collecting the crystals of the pure palonosetron.

3. The method of claim 2, wherein the collection is via filtration.

4. The method of claim 1, wherein the at least one organic solvent is selected from the group consisting of methanol, ethanol, n-propanol, isopropanol, dichloromethane, chloroform, n-pentane, n-hexane, cyclohexane, n-heptane, petroleum ether, and mixtures thereof.

5. The method of claim 4, wherein the at least one organic solvent is ethanol or a 1:1:1 mixture (by volume) of methanol: dichloromethane: petroleum ether.

* * * * *